United States Patent [19]

Huang et al.

[11] 4,136,960
[45] Jan. 30, 1979

[54] TEST APPARATUS FOR OPTICAL WAVEGUIDES

[75] Inventors: Yung-Yien Huang, Freehold; Jerzy A. Olszewski, Edison; Arnab Sarkar, Piscataway, all of N.J.

[73] Assignee: General Cable Corporation, Greenwich, Conn.

[21] Appl. No.: 765,658

[22] Filed: Feb. 4, 1977

[51] Int. Cl.² ............................................. G01N 21/32
[52] U.S. Cl. .................................... 356/239; 356/244; 356/73.1
[58] Field of Search ............... 356/201, 205, 206, 239, 356/244; 65/29, 158

[56] References Cited

U.S. PATENT DOCUMENTS 4,021,217   5/1977   Bondybey et al. .............. 356/239 X

OTHER PUBLICATIONS

Guttmann et al., "Location of Imperfections in Optical Glass-Fibre Waveguides," *Electronics Letters*, vol. 11, No. 10, pp. 216–217 5/75.

*Primary Examiner*—John K. Corbin
*Assistant Examiner*—Matthew W. Koren
*Attorney, Agent, or Firm*—Roy C. Hopgood; John M. Calimafde; Charles W. Neill

[57] ABSTRACT

This specification describes a novel apparatus and method for testing optical wave guides to determine the optical attenuation and to locate faults in the optical fiber. The light for test purposes is launched into the fiber by one or more light beams that surround the wave guides and that are focussed to converge from around the circumference and at the axis of the wave guide; the convergence being at low angles of incidence, so that some of the light enters the wave guide. The remaining light launched into the wave guide in opposite directions at a location, nearer to one end than to the other, is measured at opposite ends of the wave guide. The ratio of the light at the opposite ends of the wave guide and the difference in the length of travel of the light from the region of entry to each end is used to compute attenuation. Faults are found by internal reflections of the light beam in the wave guide.

16 Claims, 3 Drawing Figures

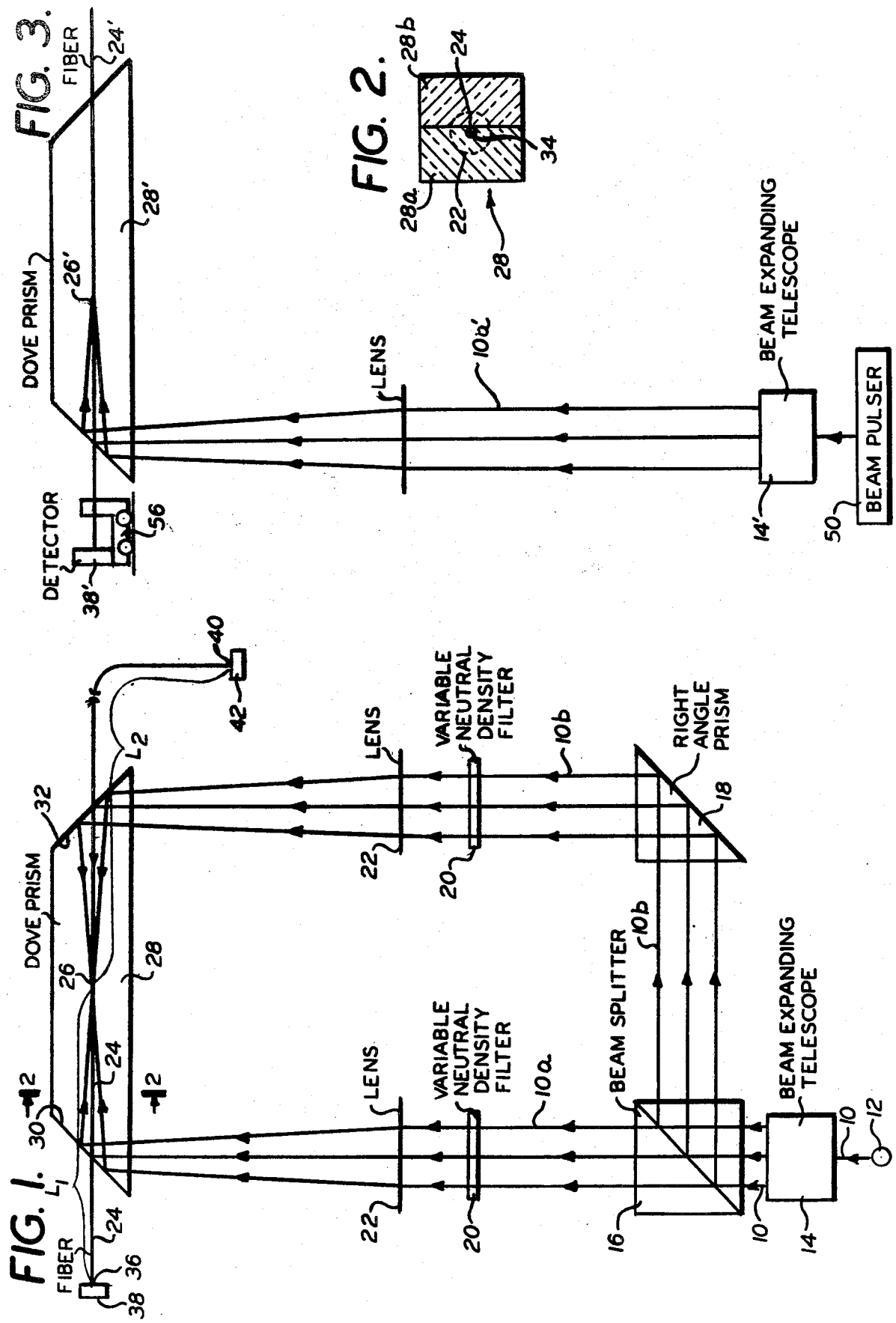

TEST APPARATUS FOR OPTICAL WAVEGUIDES

BACKGROUND AND SUMMARY OF THE INVENTION

One method of determining the attenuation in wave guides has been by launching light into fiber from one end of the fiber and measuring the output power of light at the opposite end of the fiber. A second measurement is made after cutting a short length from the input end of the fiber. The attenuation is then calculated from the two power measurements made and the length of fiber that is removed between the successive power measurements. A modification of this first method couples light from a laser into the glass fiber by way of a taper coupler; the fiber being heated and necked down at the point of coupling. A portion of the fiber is cut off, as in the first described method.

Another method uses a quick-connect-disconnect splice joint where the output power is a function of the fiber attenuation plus the loss at the joint. The coupled power is obtained by attaching a detector in the joint in place of a fiber. This method suffers from lack of inherent repeatability because of variations in position in mechanical connect-disconnect connectors and variations in geometry of fibers under measurement (varying coupling) and consequently results are not uniformly accurate.

The present invention does not require destruction of any portion of the wave guide, and the method has a light source of desired wavelength, preferably collimated, which can be passed through a collimating beam expander with or without spatial filter. The expanded light beam is passed through a beam splitter. The split beams may then be reflected by right angle prisms or mirrors, preferably through neutral density filters, and the two parallel light beams of equal or constant power ratio are passed through converging lenses and launched in opposite directions along the length of the fiber and preferably focussed on the same point at the axis of the fiber. Dove prisms are preferably used with a groove in one of the prisms to maintain the fiber in a straight line at the location where the light is launched into the fiber.

Other objects, features and advantages of the invention will appear or be pointed out as the description proceeds.

BRIEF DESCRIPTION OF DRAWING

In the drawing, forming a part hereof, in which like reference characters indicate corresponding parts in all the views:

FIG. 1 is a diagrammatic view showing the way in which a light beam from one source can be split and reflected so as to converge the beams at a common point along the longitudinal axis of an optical wave guide, the attenuation of which is to be measured;

FIG. 2 is a greatly enlarged sectional view taken on the line 2—2 of FIG. 1; and FIG. 3 is a diagrammatic view illustrating the way in which one light beam, focussed on the axis of the wave guide, can be used for detecting faults in the wave guide.

DESCRIPTION OF PREFERRED EMBODIMENT

A light beam 10 from a source 12 is passed through a beam-expanding telescope 14 to a beam splitter 16. A part of the split beam, indicated by the reference character 10a, passes through the beam splitter 16; and the other part, indicated by the reference character 10b, is directed at an angle substantially normal to the portion 10a.

A reflector, shown in FIG. 1 as a right angle prism 18, reflects the light beam 10b to a course parallel to that of the light beam 10a. The expanded light beam 10 and both of the light beams 10a and 10b are preferably collimated, and they preferably pass through variable neutral density filters 20 which can be used to equalize the intensity of the light beams, if they are not equal; or to obtain a ratio of intensity where that may be desirable in connection with the use of the light beams for measuring attenuation of the wave guide.

Beyond the filters 20, there are lenses 22 for refracting the light beam so as to focus each beam at substantially the same point along the axis of a wave guide 24. This point is indicated in FIG. 1 by the reference character 26.

In the illustrated construction, the wave guide 24 passes through a dove prism 28 which has reflecting faces 30 and 32 at its opposite ends. The reflecting face 30 reflects the light beam 10a so as to focus the light beam at the point 26; while the reflecting face 32 reflects the light beam 10b so as to focus at the same point 26. This point 26 is located on the longitudinal axis of the wave guide 24. The lenses 22 must be of substantial focal length so that the light of the beams 10a and 10b strikes the circumference of the wave guide 24 at a small angle to the axis of the wave guide, so that some of the light of the beams is launched into the wave guide. This angle should preferably be about two or three degrees to the longitudinal extent of the circumferential surface of the wave guide.

FIG. 2 is a sectional view on the line 2—2 of FIG. 1 and shows the dove prism made in two parts, 28a and 28b, which have confronting surfaces which contact with one another across their entire extent, except at a groove 34 formed in the face of the prism part 28a which confronts the prism part 28b. This groove 34 is straight and large enough to hold the wave guide 24 throughout the length of the wave guide which is contained within the dove prism, as shown in FIG. 1. Both parts 28a and 28b of the dove prism have their sloping ends in alignment, so as to form continuous reflecting faces 30 and 32. The light beam 22, where it strikes the reflecting face 30, is shown in FIG. 2 in dotted lines.

The dove prism 28 is shown in FIG. 1 as located closer to one end of the wave guide 24 than to the other end. For example, the point 26 is located at a distance $L_1$ from an end 36 of the wave guide. A light detector 38 is located in position to measure the intensity of light from the beam 10b that is launched in the wave guide in the direction of the detector 38.

The other end of the wave guide 24 is indicated by the reference character 40; and there is a light detector 42 located in position to measure the intensity of the light which comes through the end 40 of the wave guide 24. This light is from the light beam 10a, which is launched in the wave guide at the point 26 and which passes through a length of wave guide indicated by the brace marked with the reference $L_2$. It is desirable to have the wave guide 24 straight at the location where the light is launched in the wave guide, because of the importance of maintaining a low angle between the light beams and the direction of extent of the wave guide, but beyond the dove prism faces, the wave guide need not extend in a straight line, and FIG. 1 shows the right hand portion of the wave guide 24 extending around curves which are not abrupt enough to impair the travel of the light through the wave guide.

The amount of power coupled (that is, the amount of light which gets into the wave guide) depends on the precision of adjustment of the optical paths so that the focal points of both beams converge on the fiber axis and the precision of positioning of the fiber with the axis of the fiber of the wave guide substantially coincident with the axis of the optical beams, and the half conical angle of the converging optical beams.

The primary advantage of this invention is that light is launched in both directions equally, or with constant ratio, from the side of a wave guide without deforming or destroying the fiber at any point.

The amount of power reaching the detector 38 at the short end $L_1$ of the wave guide is, of course, substantially greater than the amount of light reaching the detector 42 at the end of the long length $L_2$ of the wave guide. The formula used to determine attenuation (dB/unit length) is:

$$\text{Attenuation} = \frac{10 \log \frac{P_1}{P_2}}{L_2 - L_1}$$

The logarithm is to the base 10.

$P_1$ is the light power in the short length of the wave guide and $P_2$ is the light power in the long length. $L_1$ is the short length of the wave guide and $L_2$ is the longer length.

The same principle of launching light from the side of a fiber optic wave guide may be utilized in apparatus for locating faults in the wave guide where a light signal reflected back from a fault may be detected at the short open end, as shown in FIG. 3. The optical signal in this case needs to be pulsed with a suitable repetition rate. The pulse width and its rise time will determine the resolving power of the imperfections. In this application, it is necessary to launch light in one direction only, and this can be accomplished by eliminating the beam splitter of FIG. 1 and obtaining higher power, or by blocking one beam following the beam splitter.

In FIG. 3, parts corresponding to those described in FIG. 1 are indicated by the same reference character with a prime appended. A beam pulser 50 is the only additional apparatus not shown in FIG. 1. The light beam 10a' is launched in a direction away from the detector 38', which is used to detect faults. The principle relied upon is that if the wave guide has no faults, the portion of the light beam 10a' which is launched in the wave guide 24' will travel through the wave guide away from the detector 38'. However, if there are imperfections in the wave guide 24', there will be reflections back toward the end at which the detector 38' is located.

In order to locate faults in the apparatus shown in FIG. 3, the wave guide 24' must move through the dove prism 28', so that the location of the fault moves toward the point 26' and then beyond the point 26', toward the left in FIG. 3, so that there is no further reflection of light from the fault. Means for moving the wave guide 24' and the detector 38', as a unit, as illustrated diagrammatically in FIG. 3 and indicated by the reference character 56.

It will be understood that equivalent structure can be substituted for that shown in the illustrated embodiment. For example, separate prisms or mirrors with center openings for passage of the wave guide can be used to reflect the light beams 10a and 10b in place of the dove prism. However, the dove prism has the distinct advantage that it is a unitary structure when the two halves 28a and 28b are secured together, and this insures constant angular relation of the reflectors at the opposite ends of the dove prism.

Other changes and modifications can be made in the illustrated constructions; and some features can be used in different combinations without departing from the invention as defined in the claims.

What is claimed is:

1. Apparatus for determining attenuation and the presence of faults in an optical fiber wave guide, including in combination a support holding a portion of the length of the wave guide with its axis in a straight line, a light beam source, a lens through which the light beam passes, the lens being of a nature that focusses the light along a conical pattern, and the lens being in position to direct the light beam as a converging cone of light toward a side of the wave guide intermediate the ends thereof, a reflector that directs the converging light beam with its axis substantially coincident with the axis of the wave guide, the lens having a substantial focal length so that the light of the beam strikes the sides of the wave guide at a small angle to the axis of the wave guide, so that some of the light of the beam is launched into the wave guide through the sides thereof where the wave guide is held with its axis in a straight line, and a light detector at one end of the wave guide.

2. The apparatus described in claim 1 characterized by the light beam being launched in the optical fiber wave guide through the sides of the wave guide toward one end thereof, and the light detector being located at the other end of the optical fiber wave guide for determining any light reflected back by imperfections in the wave guide.

3. The apparatus described in claim 2 characterized by a pulser for the light beam that changes the intensity of the light beam at a predetermined repetition rate for determining resolving power of the imperfections from the pulse width and its rise time.

4. The apparatus described in claim 2 characterized by means for moving the optic fiber wave guide and the light detector with respect to the location where the light is launched in the wave guide whereby variations in the light transmitted to the detector monitor uniformity of wave guide geometry and core clad interface.

5. The apparatus described in claim 1 characterized by a beam-expanding telescope that provides a column of light, the telescope being located between the source of light and the lens that focusses the beam on the axis of the optical fiber wave guide at a long focal length that brings the light into contact with the wave guide at an angle of incidence of approximately 2 to 3 degrees.

6. Apparatus for determining attenuation and the presence of faults in an optical fiber wave guide, including in combination a support holding a portion of the length of the wave guide with its axis in a straight line, a light beam source, a lens through which the light beam passes, the lens being of a nature that focusses the light along a conical pattern, and the lens having a substantial focal length so that the light of the beam strikes the wave guide at a small angle to the axis of the wave guide, so that some of the light of the beam is launched into the wave guide, a reflector in the path of the light beam between the lens and the point of focus of the lens and in position to deflect the light beam so that its point of focus is on the axis of the wave guide where the wave guide is held with its axis in a straight line, and a light detector at one end of the wave guide, characterized by a beam splitter by which the light beam is split into two light beams, the second of which is deflected at an angle to the direction of travel of the first beam, a reflector by which the second beam is again deflected in a direction toward the axis of the wave guide, a lens for focussing the second beam on the axis of the wave guide with the light from the second beam directed in the opposite direction along the wave guide to that of the first beam, and light detectors at both ends of the wave guide.

7. The apparatus described in claim 6 characterized by the lenses that focus the two light beams and the reflectors for the light beams being positioned with respect to one another to focus both light beams on the axis of the optical fiber wave guide at the same point.

8. The apparatus described in claim 6 characterized by both light beams being focussed on the optical fiber wave guide closer to one end of the wave guide than to the other, and both lenses having long focal lengths so that the light beams converge on the optical fiber wave guide at a low angle which is suffiiciently low to launch some of the light of the light beams in the wave guide.

9. The apparatus described in claim 6 characterized by one reflector for the second beam in position to bring the first and second beams into substantially parallel relation with one another and with the light of the first and second beams collimated, both of the lenses for focussing the beams being located along the beams at equal distances from the point of focus of the beams on the axis of the wave guide.

10. The apparatus described in claim 9 characterized by variable density filters in each of the light beams at locations where the first and second light beams are parallel with one another and before the light beams have passed through the lenses.

11. The apparatus described in claim 6 characterized by a dove prism that holds the optical fiber wave guide with a portion of its length in a straight line, the opposite ends of the dove prism serving as reflectors for reflecting the focussing light beams from the lenses on the axis of the optical fiber wave guide.

12. The apparatus described in claim 11 characterized by the dove prism being made in two parts, each of which has reflecting services at its opposite ends, and the reflecting surfaces at corresponding ends of the prism parts forming substantially continuous reflecting surfaces in a common plane, confronting faces on the parts of the dove prism contacting with one another continuously to make the dove prism a substantially unitary structure, and a groove in one of the confronting surfaces of a size to receive the optical fiber wave guide and to hold it with its axis in a straight line between the reflecting surfaces at the opposite ends of the dove prism.

13. The method of testing optical fiber wave guides which comprises holding a part of the length of the wave guide with its axis in a substantially straight line, passing a beam of light through a long focal length lens that converges the light beam to a cone having an included angle of approximately 4 to 6 degrees, and reflecting the light beam before it reaches its apex to bring the axis of the conical light beam into substantial alignment with the axis of the wave guide that is held in a straight line and with the apex of the beam on said axis so that light is launched in the wave guide, placing a light detector at one end of the wave guide confronting an end face of the wave guide.

14. The method described in claim 13 characterized by launching two light beams in the wave guide at substantially the same location but in opposite directions along the axis of the wave guide, the location being nearer to one end of the wave guide than to the other, measuring the light output from opposite ends of the wave guide by light detectors, and computing the attenuation of the wave guide by a relation of the ratio of the power outputs from the opposite ends of the wave guide and the differences in the lengths of the wave guide on opposite sides of the point where the light is launched in the wave guide.

15. The method described in claim 13 characterized by launching the light in the wave guide in a direction toward one end of the wave guide, placing a light detector at the opposite end of the wave guide, and detecting defects and non-uniformity of the wave guide by variations in the light reflected back to the detector at the end of the wave guide opposite to that which the light was launched.

16. The method described in claim 15 characterized by moving the wave guide with respect to the location at which the light is launched in the wave guide, pulsating the light beam that launches the light in the wave guide, and monitoring the reflected light that reaches the light detector to determine the uniformity of the wave guide and the presence of irregularities.

* * * * *